United States Patent
Ma et al.

(10) Patent No.: US 10,145,825 B2
(45) Date of Patent: *Dec. 4, 2018

(54) LUMINESCENT IRIDIUM(III) COMPLEX AND ITS USES THEREOF FOR THE G-QUADRUPLEX-BASED SWITCH-ON RAPID DETECTION OF LEAD IONS

(71) Applicants: Hong Kong Baptist University, Hong Kong (HK); University of Macau, Macau (MO)

(72) Inventors: Dik-Lung Ma, Hong Kong (HK); Sheng Lin, Hong Kong (HK); Chung-Hang Leung, Macau (MO)

(73) Assignees: Hong Kong Baptist University, Hong Kong (HK); University of Macau, Macau (MO)

( * ) Notice: Subject to any disclaimer, the term of this patent is extended or adjusted under 35 U.S.C. 154(b) by 129 days.

This patent is subject to a terminal disclaimer.

(21) Appl. No.: 15/291,041

(22) Filed: Oct. 11, 2016

(65) Prior Publication Data

US 2017/0102331 A1 Apr. 13, 2017

Related U.S. Application Data

(60) Provisional application No. 62/240,502, filed on Oct. 12, 2015.

(51) Int. Cl.
*G01N 31/22* (2006.01)

(52) U.S. Cl.
CPC ................ *G01N 31/22* (2013.01)

(58) Field of Classification Search
CPC .... G01N 31/22; G01N 21/643; G01N 21/645; G01N 2021/6417; G01N 2201/0697; G01N 2201/06113
See application file for complete search history.

(56) References Cited

U.S. PATENT DOCUMENTS

| | | | | |
|---|---|---|---|---|
| 2011/0111517 A1* | 5/2011 | Siegel | ............... | B01L 3/502707 436/164 |
| 2012/0181184 A1* | 7/2012 | Whitesides | ............. | B01L 3/502 205/775 |
| 2015/0005193 A1* | 1/2015 | Phillips | .................... | C12Q 1/26 506/11 |

FOREIGN PATENT DOCUMENTS

| | | |
|---|---|---|
| CN | 103305622 A | 9/2013 |
| CN | 103792229 A | 5/2014 |

OTHER PUBLICATIONS

Chan et al., G-quadruplexes for luminescent sensing and logic gates, 2013, 41, p. 4345-4359. (Year: 2013).*
Zhang et al., Three-dimensional paper-based electrochemiluminescence device for simultaneous detection of Pb2+ and Hg2+ based on potential-control technique, 2013, Biosensors and Bioelectronics, v. 41, p. 544-550 (Year: 2013).*
Sun et al., A suspending-droplet mode paper-based microfluidic platform for low-cost, rapid, and convenient detection of lead(II) ions in liquid solution, 2018, Biosensors and Bioelectronics, v. 99, p. 361-367 (Year: 2018).*

(Continued)

*Primary Examiner* — Lore R Jarrett
(74) *Attorney, Agent, or Firm* — Spruson & Ferguson (Hong Kong) Limited (57) ABSTRACT

A luminescent Ir(III) complex it used to develop a label-free G-quadruplex-based assay for lead ions in a liquid or aqueous solution. In particular, the present invention describes method for monitoring lead ion concentration in water.

9 Claims, 7 Drawing Sheets

Specification includes a Sequence Listing.

(56) References Cited

OTHER PUBLICATIONS

Dik-Lung Ma et. al., Group 9 Organometallic Compounds for Therapeutic and Bioanalytical Applications, Acc. Chem. Res., 2014, 47, 3614-3631.
Tao Li et. al., Lead(II)-Induced Allosteric G-Quadruplex DNAzyme as a Colorimetric and Chemiluminescence Sensor for Highly Sensitive and Selective Pb2+ Detection, Anal. Chem., 2010, 82, 1515-1520.
Shenshan Zhan et. al., Label-free fluorescent sensor for lead ion detection based on lead(II)-stabilized G-quadruplex formation, Analytical Biochemistry, 2014, 462, 19-25.
Hong-Zhang He et. al., Label-free detectionofsub-nanomolarlead(I-I)ionsinaqueoussolution using ametal-basedluminescentswitchonprobe, Biosens. Bioelectron., 2013, 41, 871-874.
Tao Li et.al., A Lead(II)-Driven DNA Molecular Device for Turn-On Fluorescence Detection of Lead(II) Ion with High Selectivity and Sensitivity, J. Am. Chem. Soc., 2010, 132, 13156-13157.
Ivan Smirnov et.al., Lead is Unusually Effective in Sequence-specific Folding of DNA, J. Mol. Biol., 2000, 296, 1-5.
Frank W. Kotch et.al., A Lead-Filled G-Quadruplex: Insight into the G-Quartet's Selectivity for Pb2+ over K+ , Org. Lett., 2000, 2, 3277-3280.
Liangqia Guo et.al., A G-quadruplex based label-free fluorescent biosensor for lead ion, Biosens. Bioelectron., 2012, 35, 123-127.

\* cited by examiner

LUMINESCENT IRIDIUM(III) COMPLEX AND ITS USES THEREOF FOR THE G-QUADRUPLEX-BASED SWITCH-ON RAPID DETECTION OF LEAD IONS

CROSS REFERENCE TO RELATED APPLICATIONS

This is a U.S. non-provisional patent application which claims benefit from U.S. provisional application No. 62/240,502 filed Oct. 12, 2015, and the disclosure of which is incorporated herein by reference.

FIELD OF INVENTION

The present invention relates to the synthesis and use of a luminescent iridium(III) complex for the construction of a label-free G-quadruplex-based assay for the rapid detection of lead ions in a liquid or aqueous solution. In particular, the present invention relates to method for monitoring lead ion concentration in water.

BACKGROUND OF INVENTION

Heavy-metal pollution has attracted much attention in the public media and scientific community due to the toxic effects of heavy metal ions on human health and the environment. The lead(II) ion, as one of the acutely toxic metal ions, is a dangerous contaminant which causes adverse health effects in humans, including delayed physical and mental developmental in infants and children, kidney disease and high blood pressure in adults. Meanwhile, certain oligonucleotides undergo conformational changes in the presence of particular heavy metal ions.

Atomic absorption spectrometry (AAS) and inductively coupled plasma mass spectrometry (ICP-MS) are widely-used instrumental techniques for lead(II) ion detection, but their sophisticated instrumentation and/or complicated sample preparation hamper their application for in-field studies. In recent years, fluorescent, colorimetric methods utilizing organic fluorescent dyes, oligonucleotides, or lead (II)-dependent RNA cleaving DNA enzymes have been developed for lead(II) ion detection. A short testing time and portable instrument or tool is required for rapid online detection of lead ions in drinking water around the standard of World Health Organization (WHO) for safe drinking water.

SUMMARY OF INVENTION

In accordance with a first aspect of the present invention, a luminescent iridium (III) (Ir(III)) complex is utilized to construct a label-free G-quadruplex-based assay for the rapid detection of lead ions in a liquid or aqueous solution. In particular, the present invention provides an application of the assay for monitoring lead ion concentration in water.

In accordance with a first aspect of the present invention, there is provided a system for detecting lead ions in a liquid or aqueous solution comprising at least one luminescent iridium(III) complex and at least one G-quadruplex-forming sequence; wherein said G-quadruplex-forming sequence is a single stranded oliogmer in the absence of lead ions and said G-quadruplex-forming sequence forms a G-quadruplex structure in the presence of lead ions and wherein said G-quadruplex-forming sequence reacts with said at least one luminescent iridium(III) complex to emit luminescent emission.

In accordance with a second aspect of the present invention, there is provided a method for detecting lead ions in a liquid or aqueous solution; introducing said aqueous solution to the G-quadruplex-forming sequence to form a first mixture; adding the luminescent iridium (III) complex to the first mixture to form a second mixture; and measuring luminescent emission of the second mixture.

In a first embodiment of the first aspect of the present invention, there is provided a system for detecting lead ions in a liquid or aqueous solution wherein said at least one luminescent iridium(III) complex is Ir(III) complex, [Ir(epyd)2(dclphen)]PF6 wherein epyd=2-(4-ethylphenyl)pyridine; dclphen=4,7-dichloro-1,10-phenanthroline.

In a second embodiment of the first aspect of the present invention, there is provided a system for detecting lead ions in a liquid or aqueous solution wherein said at least one G-quadruplex-forming sequence is PS2.M, 5'-GTGGG-TAGGGCGGGTTGG-3' (SEQ ID NO. 1).

In a third embodiment of the first aspect of the present invention, there is provided a system for detecting lead ions in a liquid or aqueous solution wherein said aqueous solution is water.

In a fourth embodiment of the first aspect of the present invention, there is provided a system for detecting lead ions in a liquid or aqueous solution wherein said luminescent emission is measured using at least one spectrometer.

In a first embodiment of the second aspect of the present invention, there is provided a method for detecting lead ions in a liquid or aqueous solution wherein said at least one luminescent iridium(III) complex is Ir(III) complex, [Ir(epyd)$_2$(dclphen)]PF$_6$ wherein epyd=2-(4-ethylphenyl)pyridine; dclphen=4,7-dichloro-1,10-phenanthroline.

In a second embodiment of the second aspect of the present invention, there is provided a method for detecting lead ions in a liquid or aqueous solution wherein said at least one G-quadruplex-forming sequence is PS2.M, 5'-GTGGG-TAGGGCGGGTTGG-3' (SEQ ID NO. 1). Said at least one G-quadruplex-forming sequence is PS2.M, 5'-GTGGG-TAGGGCGGGTTGG-3' (SEQ ID NO. 1).

In a third embodiment of the second aspect of the present invention, there is provided a method for detecting lead ions in a liquid wherein said liquid is water.

In a forth embodiment of the second aspect of the present invention, there is provided a method for detecting lead ions in a liquid or aqueous solution wherein luminescent emission is measured using at least one spectrometer.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

The present invention is not to be limited in scope by any of the specific embodiments described herein. The following embodiments are presented for exemplification only.

Without wishing to be bound by theory, the present invention provides a luminescent Ir(III) complex for constructing a label-free G-quadruplex-based assay for the rapid detection of lead ions in a liquid or aqueous solution. In particular, the present invention provides a method for monitoring lead ion concentration in water.

The lead(II) ion is known to induce the structural transition of a guanine-rich single-stranded oligonucleotide into a G-quadruplex, which is a non-canonical DNA secondary structure consisting of planar stacks of four guanines stabilized by Hoogsteen hydrogen bonding. Meanwhile, rapid advances in the field of DNA technology over the past several years have highlighted the potential use of oligonucleotides as attractive signal transducing units for the detection of biologicaland environmental important analytes. Oligonucleotides offer salient advantages in bio-sensing applications, such as their relatively small size, low cost, facile synthesis and modification, good thermal stability, and reusability. In particular, the G-quadruplex motif, which is a non-canonical DNA secondary structure composed of planar stacks of four guanines stabilized by Hoogsteen hydrogen bonding, has attracted particular interest in sensing applications. The extensive structural polymorphism of G-quadruplexes has rendered them as versatile signal-transducing elements for the development of DNA-based probes. In recent years, a number of oligonucleotide-based sensing platforms for lead ions have been developed. For example, Zhou and co-workers, China Patent CN103305622A; and Sun and co-workers, China Patent CN103792229A, have reported fluorescent assays for lead ions by utilizing G-rich oligomer and fluorescent organic dyes. The invention from Zhou and co-workers uses SYBR Green I, which is a commercially-available organic dye with low selectivity for G-quadruplex DNA, and also has narrow Stoke shifts and short lifetimes when compared to transition metal complexes. Also, SYBR Green I may be influenced by other compounds in the real water sample or organic tissues. Moreover, the assay is a switch-off method which might lead to false positive results, and also requires at least 20 minutes for measuring each sample. The other invention from Sun and co-workers employs a reaction-based system to detect lead ions, in which lead ions act as an inhibitor of a reaction. The detection limit of this invention in real water sample is unknown, and the tested value in urine could not reach the standard of World Health Organization (WHO) for safe drinking water (below 10 μg/L). Guo, Fu and co-workers, *Biosens. Bioelectron.*, 2012, 35, 123-127 have utilized a fluorescent organic dye N-methyl mesoporphyrin IX (NMM) to detect lead ions by G-quadruplex based label-free platform. In the presence of lead ions, the DNA conformation does not bind the fluorescent organic dye, leading to a switch-off response when the concentration of lead ions is increased. This method also needed 30 minutes to measure a sample. Additionally, Tao Li, Erkang Wang and Shaojun Dong, *Anal. Chem.*, 2010, 82, 1515-1520 and *J. Am. Chem. Soc.*, 2010, 132, 13156-13157 have also utilized DNA conformational change to monitor lead ions. These reports demonstrate that DNA oligonucleotides can be integrated as useful, functional and structural elements for the construction of sensitive luminescent platforms for the detection of lead ions. However, many of these methods still are unable to detect the presence of low levels of lead ions in aqueous samples. Herein, the present invention provides using luminescent transition metal complex in conjunction with a G-quadruplex-based platform (*Biosens. Bioelectron.*, 2013, 41, 871-874). This platform could be used directly on aqueous samples and the testing period is dramatically decreased to less than 10 minutes using the specified method and a portable instrument, which is a unique combination that is used in the present invention.

Figure 1:
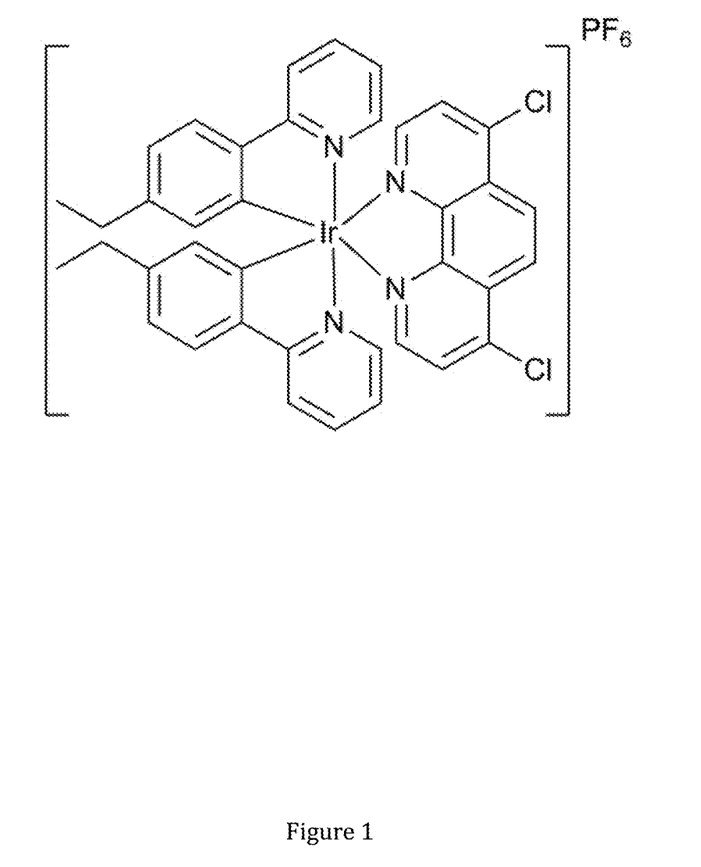
FIG. 1 shows chemical structure of the luminescent Ir(III) complex, complex 1 of the present invention.

In recent years, luminescent transition metal complexes have arisen as viable alternatives to organic dyes for sensory applications due to their notable advantages. Firstly, metal complexes generally emit in the visible region with a long phosphorescence lifetime, allowing them to be readily distinguished from a fluorescent background arising from endogenous fluorophores in the sample matrix by the use of time-resolved fluorescent spectroscopy. Secondly, the precise and versatile arrangement of co-ligands on the metal centre allows the interactions of metal complexes with biomolecules to be fine-tuned for maximum selectivity and sensitivity. Thirdly, these metal complexes often possess interesting photophysical properties that are strongly affected by subtle changes in their local environment. For example, platinum(II) (Pt(II)) and ruthenium(II) (Ru(II)) complexes have been extensively investigated as "molecular light switches" for nucleic acids, including G-quadruplex DNA. However, luminescent complexes based on the Ir(III) center have been comparatively less explored. In this invention, a luminescent Ir(III) complex is synthesised and evaluated for its ability to act as G-quadruplex-selective luminescence switch-on probe. The Ir(III) complex 1 [Ir(epyd)$_2$(dclphen)]PF$_6$ (where epyd=2-(4-ethylphenyl)pyridine; dclphen=4,7-dichloro-1,10-phenanthroline) (FIG. 1) is employed as a G-quadruplex probe for the construction of a label-free luminescent rapid detection platform for lead ions in aqueous solution. Also, the application of this platform for monitoring lead ions in water in a short time period is demonstrated. To our knowledge, no luminescent G-quadruplex-based assay for the rapid detection of lead ions in the water has yet been reported. And the metal complex of the present invention is designed with the superiority in binding G-quadruplex based on our experience of developing G-quadruplex-selectivity probe (*Acc. Chem. Res.*, 2014, 47, 3614-3631).

Results and Discussion

Principle of Luminescent G-quadruplex-based Probe for Lead Ion Detection

Figure 7:
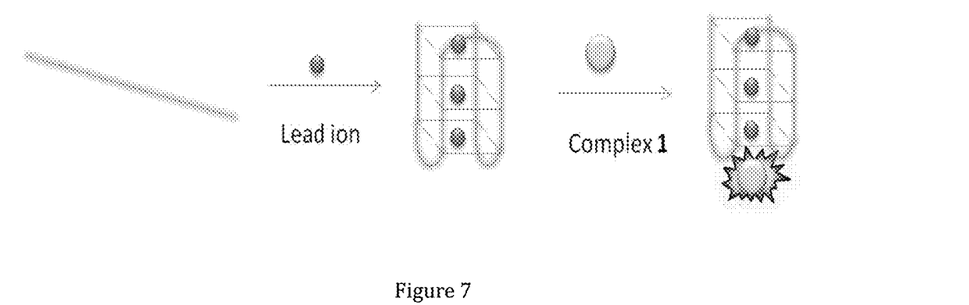
FIG. 7 shows the schematic diagram of the luminescent switch-on assay to monitor lead ions using the G-quadruplex-selective probe complex 1.

Lead ions can induce a guanine-rich single-stranded DNA (ssDNA) oligonucleotide into a G-quadruplex motif (*Org. Lett.*, 2000, 2, 3277-3280 and *J. Mol. Biol.*, 2000, 296, 1-5). The mechanism of lead ion rapid detection platform is outlined in FIG. 7. One embodiment of the present invention uses a single strand oligomer consisting of a G-quadruplex-forming sequence (PS2.M, 5'-GTGGGTAGGGCGGGTTGG-3'), which acts as a special sensor for lead ions. In the absence of lead ions, the single-strand oligonucleotide, PS2.M, will not fold into G-quadruplex structure, and remains as a single-strand structure that interacts only weakly with the luminescent Ir(III) complex. In contrast, in the presence of lead ions, PS2.M folds into a G-quadruplex structure. The nascent G-quadruplex structure is then recognized by the luminescent Ir(III) complex with an enhanced emission response, allowing the system to function as a switch-on luminescent probe for lead ions.

Verification of Ir(III) Complex 1 as G-quadruplex-selective Probe

Figure 2:
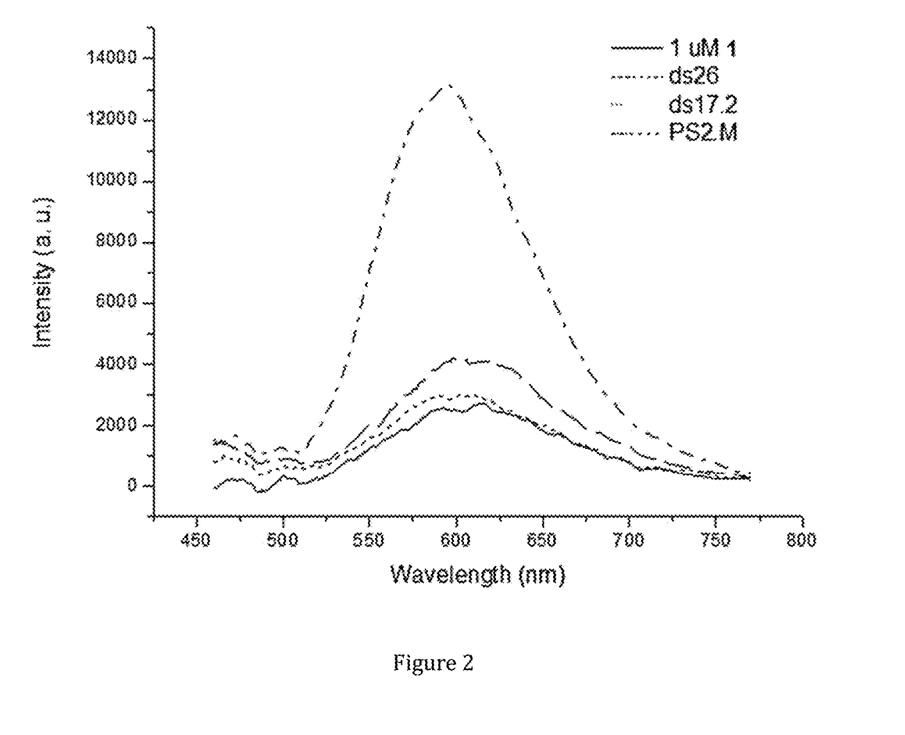
FIG. 2 shows luminescence response of complex 1 with different DNA sequences.
Figure 6:
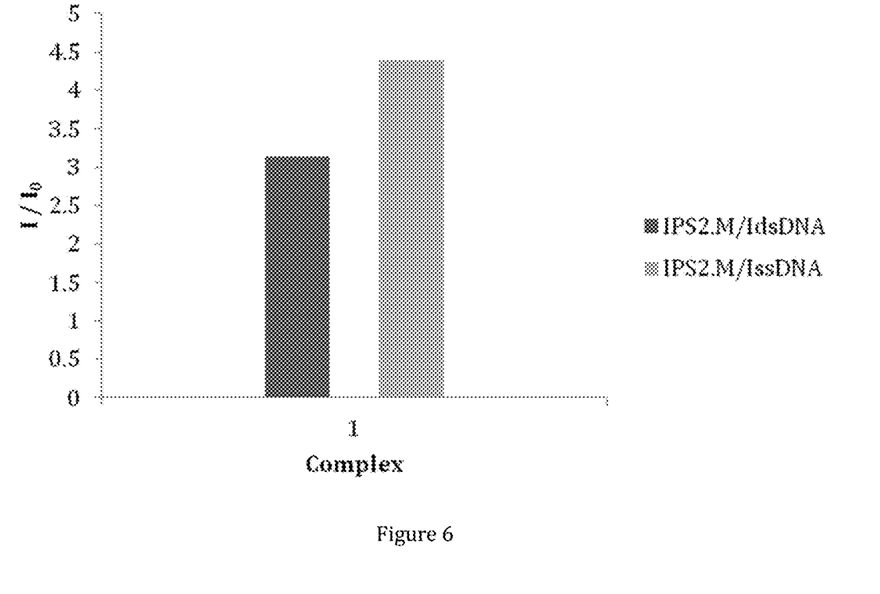
FIG. 6 shows the diagrammatic bar array representation of the luminescence enhancement selectivity ratio of complex 1 [I/I$_0$] for PS2. M G-quadruplex DNA over double strand DNA (dsDNA, ds26) and single strand DNA (ssDNA, ds17.2). [PS2. M G-quadruplex DNA over double strand DNA (dsDNA, ds26)=IPS2.M/IdsDNA and PS2. M G-quadruplex DNA over single strand DNA (ssDNA, ds17.2)=IPS2.M/IssDNA]

In the present invention, emission response of luminescent Ir(III) complex 1 (FIG. 1) to different forms of DNA, including G-quadruplex, ssDNA and dsDNA (Table S1), is shown. Complex 1 bearing the N^N ligand dclphen (4,7-dichloro-1,10-phenanthroline) and the C^N ligand epyd (2-(4-ethylphenyl)pyridine) shows a selective response for G-quadruplex DNA (FIG. 2 and FIG. 6), while not showing any luminescence enhancement towards lead ions (data not shown). This result demonstrates the ability of complex 1 to discriminate between G-quadruplex DNA, dsDNA and ssDNA. The luminescence enhancement of complex 1 in the presence of G-quadruplex DNA is believed to be due to its ability to bind to G-quadruplex structures through groove/loop binding or end-stacking interactions. This shields the complex from the aqueous solvent environment and suppresses non-radiative decay of the excited state, thus leading to enhanced triplet state emission.

Luminescent Rapid Detection of Lead Ions in Aqueous Solution

Figure 3:
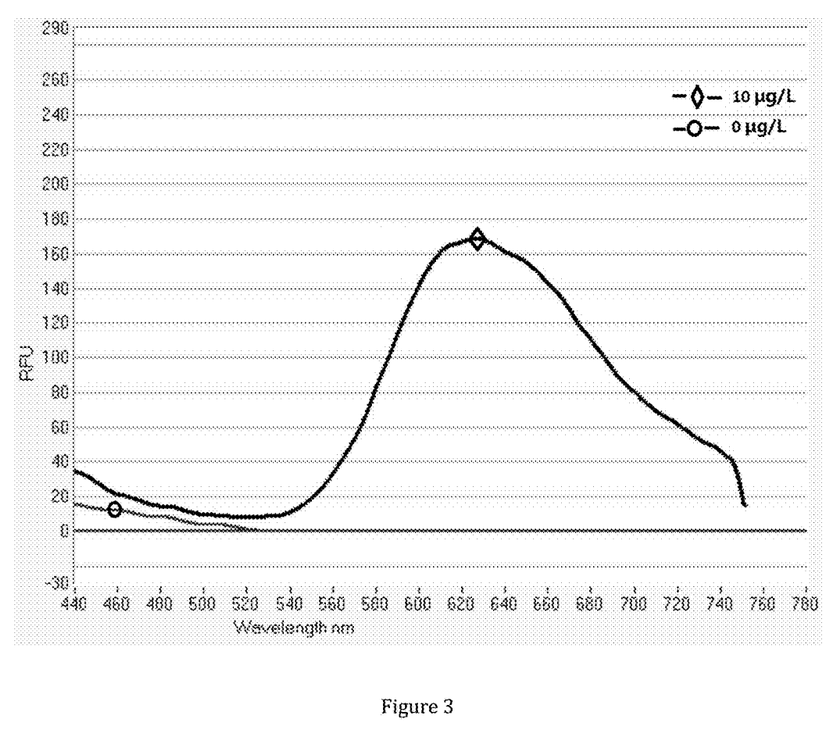
FIG. 3 shows luminescence spectra of complex 1/G4-quadruplex system in the presence of lead ions (10 μg/L) or absence of lead ions (0 μg/L) using NanoDrop 3300 spectrometer by deducting the complex 1/G4-quadruplex system background luminescence.
Figure 4:
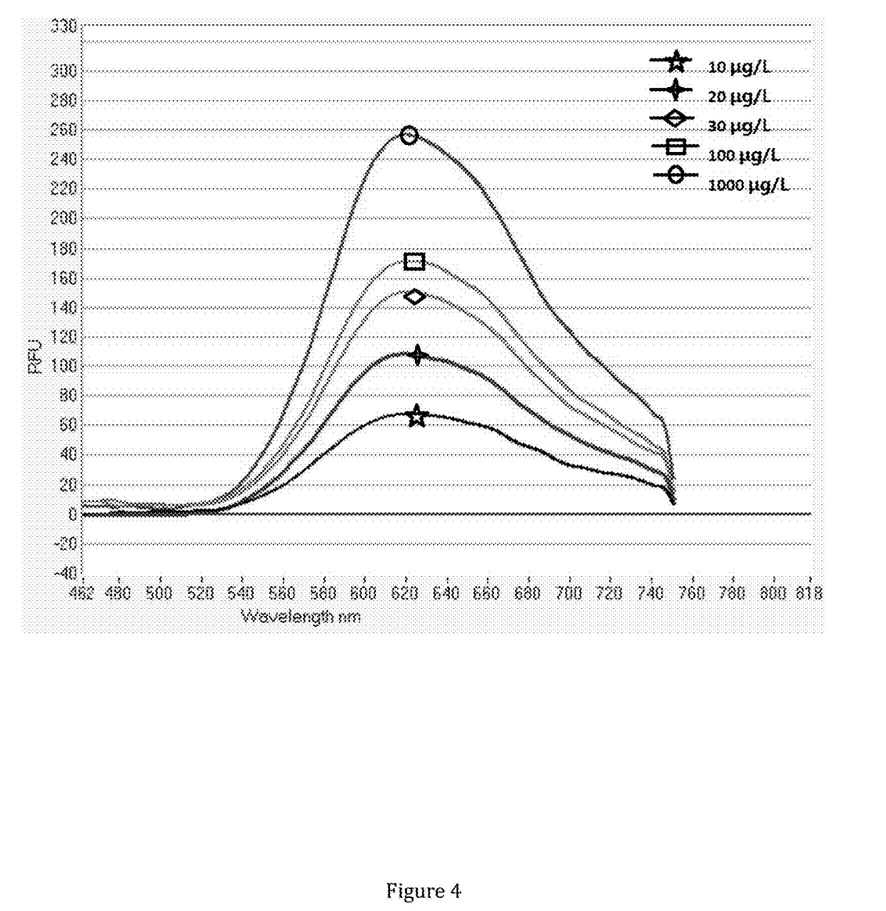
FIG. 4 shows luminescence spectra of complex 1/G4-quadruplex system in response to various concentrations of lead ions: 10, 20, 30, 100 and 1000 μg/L spiked into MiliQ™ ultrapure water using NanoDrop 3300 spectrometer by deducting the complex 1/G4-quadruplex system background luminescence.

The characterization and photophysical properties of the Ir(III) complex 1 are given in the Table S2. Given the promising G-quadruplex-selective luminescent behaviour exhibited by complex 1, one embodiment of the present invention sought to employ complex 1 as a G-quadruplex-selective probe and PS2.M as the lead ion sensor to construct a label-free luminescent rapid detection platform for lead ions in aqueous solution. The luminescence response of complex 1 and PS2.M to lead ions is shown. Upon incubation with lead ions, the luminescence of complex 1 is significantly enhanced. The luminescence enhancement of is due to the formation of the G-quadruplex of PS2.M induced structure by lead ions, which is subsequently recognized by complex 1 (FIG. 3 and FIG. 4). These results suggest that the luminescence enhancement of the system originated from the specific interaction of complex 1 with the G-quadruplex motif, PS2.M, which is generated by the structural transition of PS2.M, in the presence of lead ions.

Application of Lead Ion Detection Assay in Water

Figure 5:
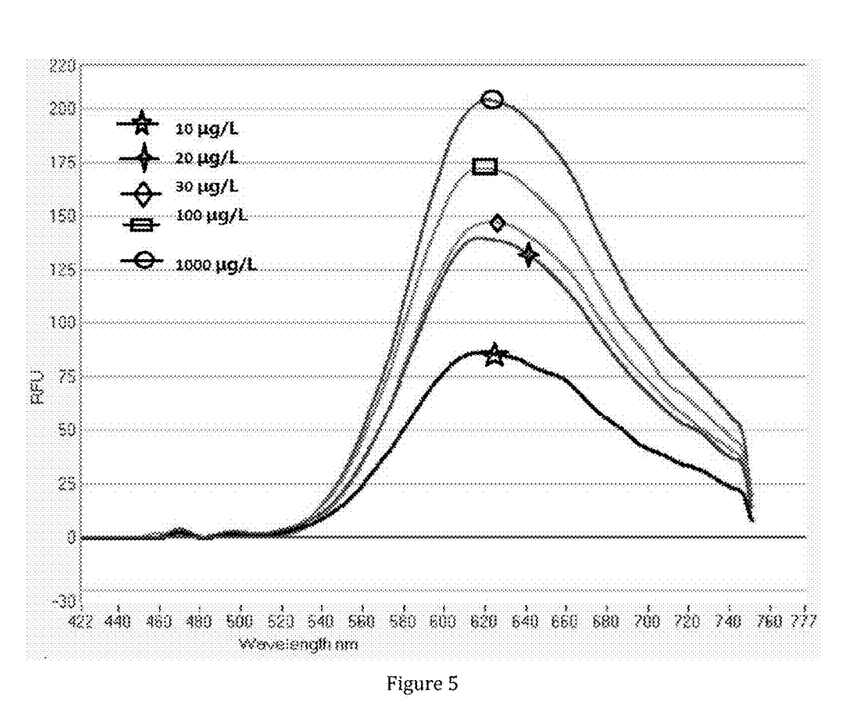
FIG. 5 shows luminescence spectra of complex 1/G4-quadruplex system in response to various concentrations of lead ions: 10, 20, 30, 100 and 1000 μg/L spiked into tap water using NanoDrop 3300 spectrometer by deducting the complex 1/G4-quadruplex system background luminescence.

The performance of the G-quadruplex-based sensing platform of the present invention to detect lead ions in tap water is shown. In a reaction system containing tap water, the present complex 1/G-quadruplex DNA system experiences a gradual increase in luminescence intensity with increase concentration of lead ions (FIG. 5). This result demonstrates that this sensing system of the present invention is useful for rapid detection of lead ions in water.

Experimental Section

Materials

Reagents, unless specified, are purchased from Sigma Aldrich (St. Louis, Mo.) and used as received. Iridium chloride hydrate ($IrCl_3 \cdot xH_2O$) is purchased from Precious Metals Online (Australia). All oligonucleotides are synthesized by Techdragon Inc. (Hong Kong, China).

General Experimental

Mass spectrometry is performed at the Mass Spectroscopy Unit at the Department of Chemistry, Hong Kong Baptist University Hong Kong (China). Deuterated solvents for Nuclear magnetic resonance (NMR) purposes are obtained from Armar and used as received.

$^1H$ and $^{13}C$ NMR are recorded on a Bruker Avance 400 spectrometer operating at 400 MHz ($^1H$) and 100 MHz ($^{13}C$). $^1H$ and $^{13}C$ chemical shifts are referenced internally to solvent shift (acetone-$d_6$: $^1H$ δ 2.05, $^{13}C$ δ 29.8; $CD_3Cl$: $^1H$ δ 7.26, $^{13}C$ δ 76.8). Chemical shifts (δ) are quoted in ppm, the downfield direction being defined as positive. Uncertainties in chemical shifts are typically ±0.01 ppm for $^1H$ and ±0.05 for $^{13}C$. Coupling constants are typically ±0.1 Hz for $^1H$-$^1H$ and ±0.5 Hz for $^1H$-$^{13}C$ couplings. The following abbreviations are used for convenience in reporting the multiplicity of NMR resonances: s, singlet; d, doublet; t, triplet; q, quartet; m, multiplet; br, broad. All NMR data is acquired and processed using standard Bruker software (Topspin).

Photophysical measurement

Emission spectra and lifetime measurements for complexes are performed on a PTI TimeMaster C720 Spectrometer (Nitrogen laser: pulse output 337 nm) fitted with a 380 nm filter. Error limits are estimated: λ (±1 nm); τ (±10%); φ (±10%). All solvents used for the lifetime measurements are degassed using three cycles of freeze-vac-thaw.

Luminescence quantum yields are determined using the method of Demas and Crosby $[Ru(bpy)_3][PF_6]_2$ in degassed acetonitrile as a standard reference solution ($\Phi_r$=0.062) and calculated according to the following equation:

$$\Phi_s = \Phi_r (B_r/B_s)(n_s/n_r)^2 (D_s/D_r)$$

where the subscripts s and r refer to sample and reference standard solution respectively, n is the refractive index of the solvents, D is the integrated intensity, and Φ is the luminescence quantum yield. The quantity B is calculated by $B = 1-10^{-AL}$, where A is the absorbance at the excitation wavelength and L is the optical path length.

Synthesis

The following complex is prepared according to (modified) literature methods. All complexes are characterized by $^1H$ NMR, $^{13}C$ NMR, high resolution mass spectrometry (HRMS) and elemental analysis.

The precursor Ir(III) complex dimer $[Ir_2(C^{\wedge}N)_4Cl_2]$ is prepared (C^N=epyd=2-(4-ethylphenyl)pyridine). Then, a suspension of $[Ir_2(C^{\wedge}N)_4Cl_2]$ (0.2 mmol) and corresponding N^N ligand dclphen (dclphen=4,7-dichloro-1,10-phenanthroline, 0.44 mmol) in a mixture of DCM:methanol (1:1, 20 mL) is refluxed overnight under a nitrogen atmosphere. The resulting solution is then allowed to cool to room temperature, and filtered to remove unreacted cyclometallated dimer.

To the filtrate, an aqueous solution of ammonium hexafluorophosphate (excess) is added and the filtrate is reduced in volume by rotary evaporation until precipitation of the crude product occurred. The precipitate is then filtered and washed with several portions of water (2×50 mL) followed by diethyl ether (2×50 mL). The product is recrystallized by acetonitrile:diethyl ether vapor diffusion to yield the titled compound.

Complex 1. Yield: 68.7%. $^1$H NMR (400 MHz, Acetone-$d_6$) δ 8.72 (d, J=1.2 Hz, 2H), 8.42 (d, J=5.6 Hz, 2H), 8.25 (d, J=5.6 Hz, 2H), 8.18 (d, J=8.0 Hz, 2H), 7.91-7.83 (m, 2H), 7.79 (d, J=0.8 Hz, 2H), 7.76 (d, J=0.8 Hz, 2H), 6.96-6.92 (m, 4H), 6.29 (d, J=1.2 Hz, 2H), 2.43 (d, J=7.6 Hz, 4H), 1.03 (t, J=7.6 Hz, 6H); $^{13}$C NMR (100 MHz, Acetone-$d_6$) 168.7, 152.7, 150.5, 148.9, 147.4, 145.7, 142.8, 139.4, 131.9, 131.0, 128.7, 126.3, 125.8, 123.8, 123.4, 120.4, 29.8, 15.5; MALDI-TOF-HRMS: Calcd. for $C_{38}H_{30}Cl_2IrN_4[M-PF_6]^+$: 805.1477 Found.: 805.5739; Anal.: $(C_{38}H_{30}Cl_2IrN_4PF_6+2H_2O)$ C, H, N: calcd. 46.25, 3.47, 5.68; found. 46.04, 3.11, 5.67.

Luminescence Response of Ir(III) Complex 1 Towards Different Forms of DNA

The G-quadruplex DNA-forming sequence (PS2. M), dsDNA or ssDNA is annealed in Tris-HCl buffer (10 mM Tris, 100 mM KCl, pH 7.1) and is stored at −20° C. before use. Complex 1 (1 μM) is added to 5 μM of ssDNA, dsDNA or PS2. M G-quadruplex DNA in Tris-HCl buffer (10 mM Tris, pH 7.1). Emission spectra are recorded in the 460-770 nm range using an excitation wavelength range of between 200-400 nm using PTI TimeMaster C720 Spectrometer.

Luminescent Rapid Detection of Lead Ions in Aqueous Solution

1 μL of ultrapure water sample with different concentrations of spiked lead ions and 1 μL of the G-quadruplex DNA-forming sequence (PS2. M: 5'-GTGGGTAGGGCGGGTTGG-3', 100 μM) are added to 8 μL of Tris buffer (10 mM Tris, pH=7.9) in a microtube;

1 μL of pure water sample and 1 μL of the G-quadruplex DNA-forming sequence (PS2. M, 100 μM) are added to 8 μL of Tris buffer (10 mM Tris, pH=7.9) in a microtube, which was used as a blank sample;

The mixtures of blank and tap water samples were annealed at least 1 minute under temperature ranging between 32° C. to 99° C., preferably 32.1° C. to 98.6° C.;

After heating, blank and tap water samples are then cooled down for at least 30 seconds under temperature ranging between −18° C. to 32° C. Meanwhile, the Nano-Drop 3300 spectrophotometer is initiated;

0.3 μL of designed probe, Ir(III) complex, (0.5 μM) is added into blank sample. After mixing, 1-2 μL of the mixed solution is put onto the sample pool of NanoDrop 3300 spectrometer for blank correction;

0.3 μL of designed probe, Ir(III) complex, (0.5 μM) is added into tap water sample. After mixing, 1-2 μL of mixed solution is put onto the sample pool of NanoDrop 3300 spectrometer for measurement. Emission spectra are recorded in the 440-750 nm range using an excitation wavelength range of between 200-400 nm. The peak demonstrates the exceeding level of lead ions in spiked ultrapure water sample (FIG. 3 and FIG. 4).

Application of Lead Ion Rapid Detection Assay in Monitoring Drinking Water 1-1.5 mL of water sample is collected from tap water;

1 μL of tap water sample with different concentrations of lead ions and 1 μL of the G-quadruplex DNA-forming sequence (PS2. M: 5'-GTGGGTAGGGCGGGTTGG-3', 100 μM) are added to 8 μL of Tris buffer (10 mM Tris, pH=7.9) in microtube;

1 μL of pure tap water sample and 1 μL of the G-quadruplex DNA-forming sequence (PS2. M, 100 μM) are added to 8 μL of Tris buffer (10 mM Tris, pH=7.9) in microtube, which is used as a blank sample;

The mixtures of blank and tap water samples are annealed at least 1 minute under temperature ranging between 32° C. to 99° C., preferably 32.1° C. to 98.6° C.;

After heating, blank and tap water samples are then cooled down for at least 30 seconds under temperature ranging between −18° C. to 32° C. Meanwhile, the Nano-Drop 3300 spectrophotometer is initiated;

0.3 μL of designed probe, Ir(III) complex 1, (0.5 μM) is added into blank sample. After mixing, 1-2 μL of mixed solution is put onto the sample pool of NanoDrop 3300 spectrometer for blank correction;

0.3 μL of designed probe, Ir(III) complex 1, (0.5 μM) is added into tap water sample. After mixing, 1-2 μL of mixed solution is put onto the sample pool of NanoDrop spectrometer for measurement. Emission spectra are recorded in the 440-750 nm range using an excitation wavelength range of between 200-400 nm. The peak demonstrates the exceeding level of lead ions in tap water (FIG. 5).

TABLE S1

DNA sequences used in the present invention:

| | Sequence |
|---|---|
| PS2.M | 5'-GTGGGTAGGGCGGGTTGG-3' (SEQ ID No. 1) |
| ds26 | 5'-CAATCGGATCGAATTCGATCCGATTG-3' (SEQ ID No. 2) |
| ds17.2 | 5'-GGGTTACTACGAACTGG-3' (SEQ ID No. 3) |

TABLE S2

Photophysical properties of Ir(III) complex 1.

| Complex | Quantum yield | $\lambda_{em}$/nm | Lifetime/μs | UV/vis absorption $\lambda_{abs}$/nm (ε/ $dm^3 \cdot mol^{-1} \cdot cm^{-1}$) |
|---|---|---|---|---|
| 1 | 0.063 | 639 | 4.577 ± 5.090 × $10^{-3}$ | 267 (7.95 × $10^3$) |

Summaries

The ability of luminescent Ir(III) complex containing epyd C^N and dclphen N^N ligands to act as a G-quadruplex probe is shown. The Ir(III) complex 1 s discovered to be a G-quadruplex-selective luminescent probe, and a label-free luminescent assay for lead ions is provided in the present invention utilizing the G-quadruplex-selective property of complex 1. Compared to conventional radiographic or luminescent assays that require multiple steps and/or the use of isotopically or fluorescently labeled nucleic acids, the present invention's label-free approach is more time and cost-effective as expensive and tedious pre-labeling or immobilization steps are avoided. On the other hand, the labeling of an oligonucleotide with a fluorophore may disrupt the interaction between the oligonucleotide with its cognate target. Finally, the present invention provides a label-free DNA-based detection platform employing luminescent transition metal complexes, which offer several advantages compared to the relatively more popular organic fluorophores, such as long phosphorescence lifetimes, large Stokes shift values and modular syntheses. Additionally, the present invention is shown to effectively detect lead ions in tap water. The present invention's novel switch-on, label-free G-quadruplex-based luminescent detection method for lead ions is a useful tool in environment and water safety monitoring.

INDUSTRIAL APPLICABILITY

The present invention relates to the synthesis and use of a luminescent Ir(III) complex as a label-free G-quadruplex-based assay for the detection of lead ions in a liquid or aqueous solution. In particular, the present invention describes a method for monitoring lead ions in drinking water.

If desired, the different functions discussed herein may be performed in a different order and/or concurrently with each other. Furthermore, if desired, one or more of the above-described functions may be optional or may be combined.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

Citation or identification of any reference in this section or any other section of this document shall not be construed as an admission that such reference is available as prior art for the present application.

What we claim is:

1. A system for detecting lead ions in a liquid comprising:
   at least one luminescent iridium(III) complex and
   at least one G-quadruplex-forming sequence;
   wherein said at least one G-quadruplex-forming sequence is a single stranded oliogmer in the absence of lead ions and said at least one G-quadruplex-forming sequence forms a G-quadruplex structure in the presence of lead ions and wherein said at least one G-quadruplex-forming sequence reacts with said at least one luminescent iridium(III) complex to emit luminescent emission and wherein said at least one luminescent iridium(III) complex is Ir(III) complex, [Ir(epyd)$_2$(dclphen)]PF$_6$, wherein epyd =2-(4-ethylphenyl)pyridine; and dclphen =4,7-dichloro-1,10-phenanthroline.

2. The system according to claim 1 wherein said at least one G-quadruplex-forming sequence is PS2.M, 5'-GTGGG-TAGGGCGGGTTGG-3' (SEQ ID NO. 1).

3. The system according to claim 1 wherein said liquid is water.

4. The system according to claim 1 further comprising at least one spectrometer for measurement of said luminescent emission.

5. A method for detecting lead ions in a liquid comprising:
   providing the system of claim 1;
   introducing said liquid to the at least one G-quadruplex-forming sequence to form a first mixture;
   adding the at least one luminescent iridium(III) complex to the first mixture to form a second mixture; and
   measuring luminescent emission of the second mixture.

6. The method of claim 5 further comprising incubating the first mixture at temperature of 32° C. to 99° C. and cooling the first mixture at −18° C. to 32° C.

7. The method according to claim 5 wherein said at least one G-quadruplex-forming sequence is PS2.M, 5'-GTGGG-TAGGGCGGGTTGG' (SEQ ID NO. 1).

8. The method according to claim 5 wherein said liquid is water.

9. The method according to claim 5 wherein luminescent emission is measured using at least one spectrometer using an excitation wavelength range of between 200-400 nm and a emission spectrum is recorded in a wavelength of 460-770 nm.

* * * * *

SEQUENCE LISTING

```
<160> NUMBER OF SEQ ID NOS: 3

<210> SEQ ID NO 1
<211> LENGTH: 18
<212> TYPE: DNA
<213> ORGANISM: artificial sequence
<220> FEATURE:
<223> OTHER INFORMATION: synthesized

<400> SEQUENCE: 1
gtgggtaggg cgggttgg                                                   18

<210> SEQ ID NO 2
<211> LENGTH: 26
<212> TYPE: DNA
<213> ORGANISM: artificial sequence
<220> FEATURE:
<223> OTHER INFORMATION: synthesized

<400> SEQUENCE: 2
caatcggatc gaattcgatc cgattg                                          26

<210> SEQ ID NO 3
<211> LENGTH: 17
<212> TYPE: DNA
<213> ORGANISM: artificial sequence
<220> FEATURE:
<223> OTHER INFORMATION: synthesized

<400> SEQUENCE: 3
gggttactac gaactgg                                                    17
```